(12) United States Patent
Patil

(10) Patent No.: US 7,847,030 B2
(45) Date of Patent: Dec. 7, 2010

(54) DIPHENYLAMINE FUNCTIONALIZATION OF POLY-α-OLEFINS

(75) Inventor: Abhimanyu O. Patil, Westfield, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 212 days.

(21) Appl. No.: 12/074,187

(22) Filed: Feb. 29, 2008

(65) Prior Publication Data

US 2009/0221760 A1 Sep. 3, 2009

(51) Int. Cl.
- C07C 211/55 (2006.01)
- C07C 2/08 (2006.01)
- C07C 2/06 (2006.01)
- C08F 8/02 (2006.01)
- C08F 8/32 (2006.01)

(52) U.S. Cl. ............ 525/333.7; 525/379; 564/409; 564/433; 508/563; 585/422; 585/446

(58) Field of Classification Search ............ 508/563; 525/333.7, 379; 564/409, 433; 585/422, 585/446, 455, 456, 457, 459, 462, 465

See application file for complete search history.

(56) References Cited

U.S. PATENT DOCUMENTS

| | | | |
|---|---|---|---|
| 5,171,915 A | 12/1992 | Forbus et al. | |
| 5,254,274 A | 10/1993 | Ho et al. | |
| 6,932,878 B1 * | 8/2005 | Hallam et al. | 149/19.91 |
| 7,145,038 B1 | 12/2006 | Hobbs | |
| 7,189,875 B2 | 3/2007 | Duyck et al. | |
| 2004/0211113 A1 * | 10/2004 | Duyck et al. | 44/426 |
| 2005/0051438 A1 * | 3/2005 | Pitner et al. | 205/413 |

FOREIGN PATENT DOCUMENTS

WO    WO 95/21871 A1 * 8/1995
WO    WO 02/079269 A1   10/2002

OTHER PUBLICATIONS

Azarbaycan Neft Tasarrufati (1986), (5), 35-7; CODEN: AZNKAY; ISSN: 0365-8554.

* cited by examiner

*Primary Examiner*—Roberto Rabago
(74) *Attorney, Agent, or Firm*—Robert A. Migliorini

(57) ABSTRACT

Provided is a process for making a diphenylamine-functionalized poly-α-olefin. The process has the following step: reacting an amount of a poly-α-olefin having a terminal double bond with a diphenylamine in the presence of a catalyst. The poly-α-olefin has a terminal double bond having a number average molecular weight of 120 to 600. The ratio of poly-α-olefin to diphenylamine is 1.0:1.0 to 10.0:1.0. Provided is also a diphenylamine-functionalized poly-α-olefin product.

15 Claims, 5 Drawing Sheets

DIPHENYLAMINE FUNCTIONALIZATION OF POLY-α-OLEFINS

FIELD

The present disclosure relates to diphenylamine functionalization of poly-α-olefins having a terminal double bond. The present disclosure further relates to diphenylamine functionalization of poly-α-olefins catalyzed with ionic liquids. The present disclosure still further relates to diphenylamine-functionalized poly-α-olefins.

BACKGROUND

Poly-α-olefins (PAOs) are used in the industry as base stocks for functional fluids, such as lubricants and transmission fluids. PAOs have conventionally been prepared by polymerization of α-olefins using a Friedel-Crafts catalyst, such as $BF_3$ or $AlCl_3$. PAOs have also been prepared by supported, reduced chromium catalysts, Ziegler-Natta or metallocene catalysts. The polymer product typically contains one terminal unsaturation per polymer chain. PAOs typically are then hydrogenated to stabilize the polymer against oxidation and degradation.

A drawback in using PAOs is their lack of compatibility with common polar additives, such as antioxidants, anti-rust agents and anti-wear agents. Conventionally, expensive polar organic esters have been added to PAO lubricants to render them compatible. Useful commercial formulations may contain 20% or more of such esters to achieve a fully homogeneous lubricant blend. Examples of such esters include, for example, bis-tridecanol adipate and pentaerythritol hexanoate. Due to the expense of such esters, it would desirable to eliminate the need for them.

Commercial PAO production processes commonly generate a distillate byproduct that has the following: (I) contains mostly $C_8H_{16}$ to $C_{30}H_{60}$ oligomers (average $C_{20}H_{40}$), (II) exhibits a relatively low average molecular weight, typically about 280, and (III) contains terminal olefin in the amount of at least about 25%. The distillate byproduct, which may amount to several percent of total PAO production, has little value at present. Thus, there is a need in the industry to develop a valuable use for the PAO distillate byproduct.

Alkylated diarylamines, such as alkylated diphenylamines, are known to be effective as stabilizers and/or antioxidants in a wide variety of organic materials, such as mineral oil-derived lubricants and synthetic lubricants.

It would be desirable to have a PAO product that could be synthesized from the distillate by product. It would be desirable to have a PAO product in which polar additives are soluble or miscible.

SUMMARY

According to the present disclosure, there is a process for making a diphenylamine-functionalized poly-α-olefin. The process has the following step: reacting an amount of a poly-α-olefin having a terminal double bond with a diphenylamine in the presence of a catalyst. The poly-α-olefin has a terminal double bond having a number average molecular weight of about 120 to about 600. The ratio of poly-α-olefin to diphenylamine is about 1.0:1.0 to about 10.0:1.0. The diphenylamine is represented by the following structure:

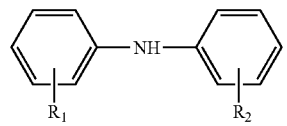

wherein $R_1$ and $R_2$ are, independently, a hydrogen or an alkyl group of 1 to 12 carbons or an aryl group of 1 to 12 carbons.

Further according to the present disclosure, there is a diphenylamine-functionalized poly-α-olefin product having the following structure:

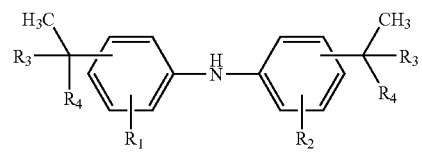

wherein $R_1$ and $R_2$ are, independently, hydrogen, an alkyl group of 1 to 12 carbons, or an aryl group of 1 to 12 carbons; and wherein $R_3$ and $R_4$ are, independently, an alkyl group of 8 to 30 carbons or an aryl group of 8 to 30 carbons.

These and other features and attributes of the disclosed process for making a diphenylamine-functionalized poly-α-olefin of the present disclosure and their advantageous applications and/or uses will be apparent from the detailed description which follows, particularly when read in conjunction with the figures appended hereto.

BRIEF DESCRIPTION OF DRAWINGS

To assist those of ordinary skill in the relevant art in making and using the subject matter hereof, reference is made to the appended drawings, wherein.

DETAILED DESCRIPTION

Figure 1:
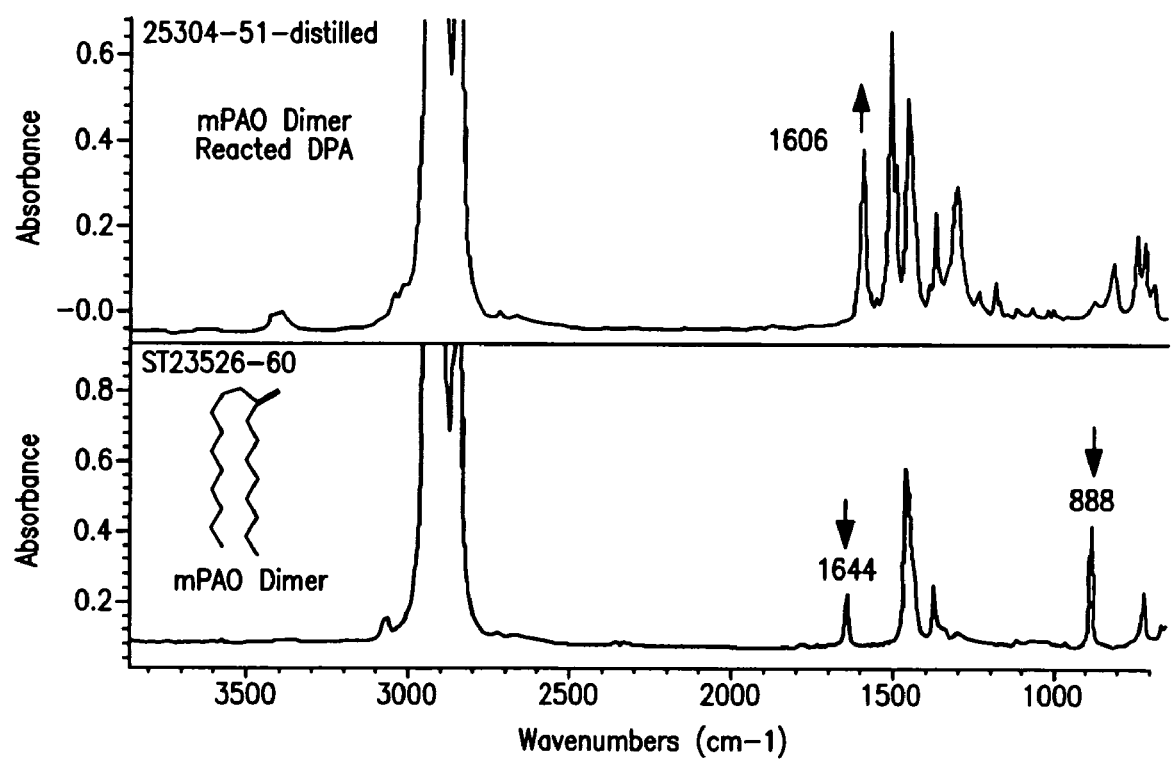
FIG. 1 is a representation of FTIR Spectra of a PAO dimer and a diphenylamine-functionalized PAO dimer product of the present disclosure.

All numerical values within the detailed description and the claims herein are understood as modified by "about." The process of the present disclosure provides for diphenylamine functionalization of olefin oligomers, including those obtained from PAO distillate byproduct or fractions thereof. Olefin oligomers useful in the process range predominantly from $C_8H_{16}$ to $C_{30}H_{60}$ (average $C_{20}H_{40}$), exhibiting a molecular weight in the range of 120 to 600.

The process of the present disclosure is represented, by way of example, in the following reaction sequence:

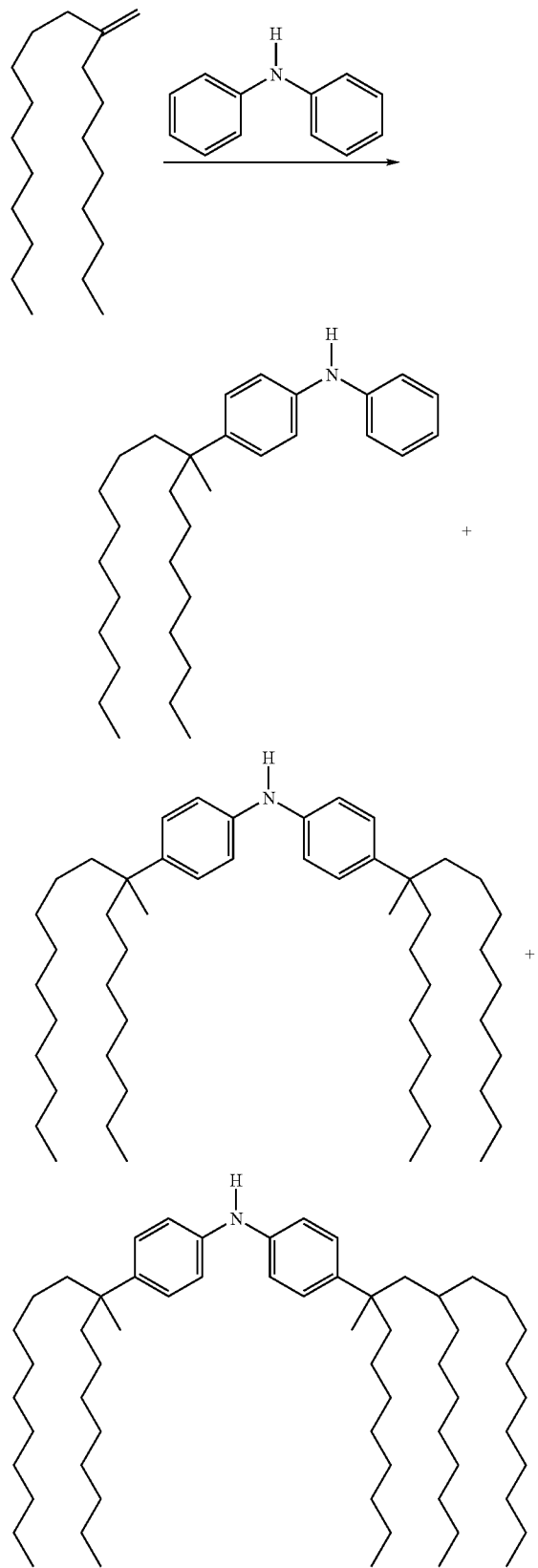

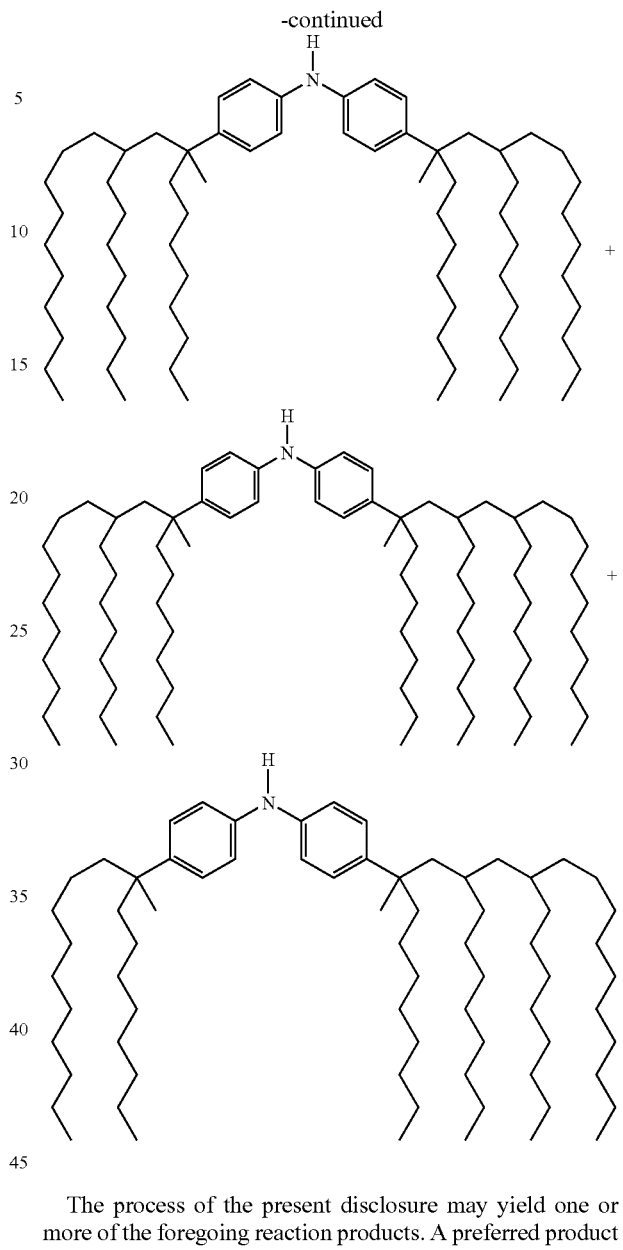

The process of the present disclosure may yield one or more of the foregoing reaction products. A preferred product is a mixture of PAO dimers monofunctionalized and difunctionalized with diphenylamine. Use of substituted diphenylamines in the process will yield analogously substituted reaction products. The oligomer with the terminal double bond represented as a reaction ingredient is illustrative. Useful oligomers will vary as disclosed herein, i.e., $C_8H_{16}$ to $C_{30}H_{60}$.

The reaction can be carried out over a wide range of temperatures and is carried out at a temperature sufficient to effect reaction. The temperature will preferably be 25° C. to 195° C., more preferably 55° C. to 175° C., and most preferably 95° C. to 165° C. The reaction can be carried out at a single temperature or, sequentially, at different temperatures.

The reaction can likewise be carried out over a wide range of pressures and is carried out at a pressure sufficient to effect reaction. The reaction pressure will preferably be 250 psi (1.72 MPa) or less and more preferably be 25 to 100 psi (0.17 to 0.69 MPa).

Inert gas, such as nitrogen, can be used to minimize oxidation of products during reaction and to allow operation at higher temperatures with oligomers of low boiling points. An atmosphere of nitrogen or other inert gas, in contrast to air, suppresses the formation of products that may deactivate the catalysts, particularly clay catalysts. Other benefits of nitrogen or other inert gas pressure include higher rates of reaction, shorter reaction times, and enhanced formation of dialkylated DPA. The loss of volatiles during reaction is reduced.

The molar ratio of PAO to diphenylamine is normally in the range of 1.0:1.0 to 10.0:1.0, preferably 1.0:1.0 to 4.0:1.0, more preferably in the range of 1.25:1.0 to 3.0:1.0, and most preferably in the range of 1.5:1.0 to 2.8:1.0. The mole ratio chosen for the reaction will affect the degree of diphenylamine conversion to alkylate.

If desired, the reaction can be carried out in a neutral solvent such as mineral oil or an inert hydrocarbon solvent, but usually no solvent is necessary.

Reaction time is a very flexible reaction parameter and is dependent on the reaction temperature, mole ratio of reactants and catalysts, and pressure. The reaction will preferably be carried out over a period of 2 to 30 hours, more preferably over a period of 5 to 24 hours, and most preferably over a period of 6 to 16 hours.

Upon completion of the reaction, the desired alkylated diphenylamine products can be isolated using conventional techniques, such as filtration, stripping under vacuum, or separation by elution with hexane using column chromatography. The diphenylamine-substituted product is preferably liquid at room temperature and atmospheric pressure.

The PAO will have a number average molecular weight of 120 to 600, preferably in the range of 150 to 400, and more preferably in the range of 160 to 280. Molecular weight of the PAO is important in yielding an end product alkylate that exhibits desirable viscosity for important applications, such as lubricants.

The distillate byproduct useful as feedstock for the process of the present disclosure will typically be a mixture of oligomers of $C_8H_{16}$ to $C_{30}H_{60}$ (average $C_{20}H_4O$), some of which have terminal double bonds and some of which that do not. Desirably, the feedstock will have a predominant proportion with terminal double bonds so that yield will be high. The distillate byproduct will preferably have a double bond content of at least 25%, more preferably 25% to 95%, still more preferably 40% to 95%, and yet more preferably in the range of 60% to 90%.

The process of the present disclosure employs a catalyst. The catalyst can be selected from the group consisting of the following: one or more Friedel-Crafts catalysts; protonic acid (Bronsted acid) catalysts, such as sulfuric acid, hydrochloric acid, and phosphoric acid; Amberlyst 15 (styrene-divinylbenzene polymer of Rohm & Haas, Co.); strongly acidic ion-exchange resins, such as Dowex 50W (The Dow Chemical Company); solid acid catalysts, such as zeolites (such as MCM22 and ZMS-48), acid clays, and amorphous solid acid catalysts (such as $WO_x/ZrO_2$ and silica-aluminate); ionic liquid catalysts; and any combination of the foregoing.

Useful clay catalysts include commercially available clay catalysts, including the following: Filtrol™ and Retrol™ available from Engelhard; Fulcat™ 14, Fulmont™ 700C, Fulmont™ 237, and Fulcat™ 22B available from Laporte Industries; and Katalysator™ K10 available from Sud-Chemi. These clays may include acid-activated or acid-leached clays. The clay catalysts may contain some water as received or water may be removed prior to use by heating with a nitrogen sweep or with vacuum stripping. Acid-activated clays are preferred. However, Lewis Acids such as $AlCl_3$ or $BF_3$, and $BF_3$ complexes of diethyl ether, phenol, including mixtures thereof with clay could be used as well. A preferred catalyst is Engelhard F-24 acid-activated clay (formerly Filtrol's Retrol clays).

Preferred catalysts are Engelhard clay F-24 catalyst and acidic ionic liquids. Useful acidic ionic liquids have at least two components. The first component is an acidic compound. The second component is an ionic liquid.

The acidic compound is selected from among one or more aluminum halides, one or more alkyl aluminum halides, and any combination thereof. For example, the first component may be aluminum trichloride, aluminum bromide, iron (III) chloride, zinc chloride, and boron trifluoride.

The ionic liquid is a salt or mixture of salts which melts below room temperature and exhibits substantially no measurable vapor pressure below the point of thermal decomposition. Ionic liquids may be characterized by the general formula $Q^+A^-$, where is $Q^+$ is quaternary ammonium, quaternary phosphonium, quaternary sulfonium, and $A^-$ is a negatively charged ion such as $Cl^-$, $Br^-$, $OCl_4^-$, $NO_3^-$, $BF_4^-$, $BCl_4^-$, $PF_6^-$, $SbF_6^-$, $AlCl_4^-$, $CuCl_2^-$, and $FeCl_3^-$. Useful liquid salts include one or more hydrocarbyl-substituted ammonium halides, hydrocarbyl-substituted imidazolium halides, hydrocarbyl-substituted pyridinium halides, and hydrocarbyl-substituted phosphonium halides. Examples of liquid salts include 1-ethyl-3-methyl-imidazolium chloride, 1-butyl-3-methylimidazolium hexafluorophosphate, and trihexyl (tetradecyl) phosphonium chloride.

The mole ratio of the acid compound to the ionic liquid preferably ranges from 1:1 to 5:1 and more preferably from 1:1 to 2:1.

Following completion of the reaction, the organic layer containing the PAO product and the unreacted low molecular weight feed is separated from the ionic liquid phase. The acidic ionic liquid catalyst that remains after recovery of the organic phase may be recycled to the reaction, if desired.

Examples of useful second components for the acidic ionic liquid are shown in structures (I) to (VI) below.

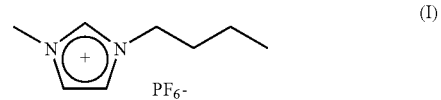

(I)

1-Butyl-3-methylimidazolium hexafluorophosphate [bmim⁺][PF$_6^-$];

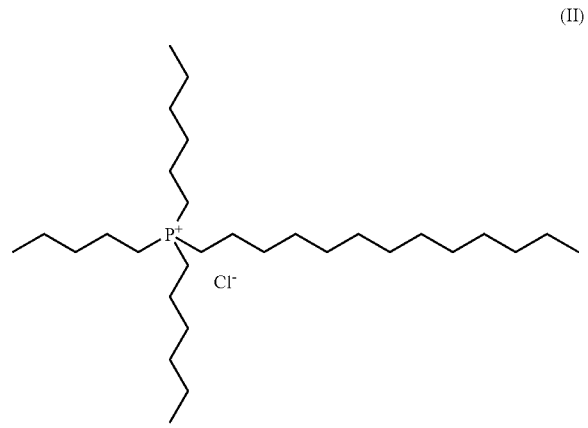

(II)

Trihexyl (tetradecyl) phosphonium chloride [thtdPh⁺][Cl⁻];

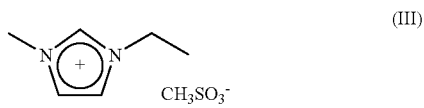
(III)

1-Ethyl-3-methylimidazolium methanesulfonate [emim⁺][CH₃SO₃⁻];

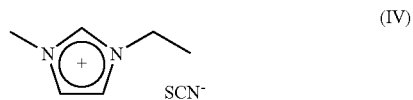
(IV)

1-Ethyl-3-methylimidazolium thiocyanate [emim⁺][SCN⁻];

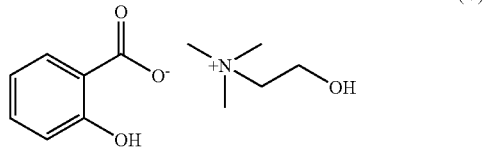
(V)

choline Salicylate; and

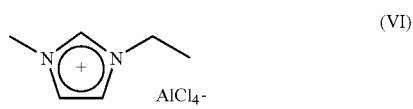
(VI)

1-Ethyl-3-methylimidazolium tetrachloroaluminate [emim⁺][AlCl₄⁻].

Other ionic liquids that can be used as second components in the acidic ionic liquids include the following:
1-Butyl-3-methylimidazolium hexafluorophosphate [bmim] [PF₆⁻];
1-Hexyl-3-methylimidazolium dioctylsulfosuccinate [hmim][doss⁻];
1-Hexyl-3-methylimidazolium hexafluoroborate [hmim] [BF₄⁻];
1-Hexyl-3-methylimidazolium hexafluorophosphate [hmim] [PF₆⁻];
tetrabutyl ammonium dioctylsulfosuccinate [tbam][doss⁻];
tetrabutyl phosphonium dioctylsulfosuccinate [tbPh][doss⁻];
tributyl (tetradecyl) phosphonium dodecylbenzenesulfonate [tbtdPh][dbs⁻];
tributyl (tetradecyl) phosphonium methanesulfonate [tbtdPh][mes⁻];
trihexyl (tetradecyl) phosphonium bis(trifluoromethane) sulfonylimide [thtdPh][Tf₂N⁻];
trihexyl (tetradecyl) phosphonium chloride [thtdPh][Cl⁻];
trihexyl (tetradecyl) phosphonium decanoate [thtdPh] [deca⁻];
trihexyl (tetradecyl) phosphonium dodecylbenzenesulfonate [thtdPh][dbs⁻]; and
trihexyl (tetradecyl) phosphonium methanesulfonate [thtdPh][mes⁻].

The process of the present disclosure affords a number of advantages. They include, for example, the following: (1) a utility for a previously wasted feedstock (the distillate) in that dimers and other low molecular weight oligomers can be converted to higher molecular weight and higher viscosity products; (2) the reaction can be carried out at a high conversion level due to the presence of the terminal double bond in the PAO; (3) the product is typically in a liquid form rather than the solid form of conventional olefins; (4) the reaction can be carried out at mild, relatively low temperatures, which affords better control of fragmentation; (5) the resultant product does not need an additional hydrogenation step to obtain stable PAO; and (6) a means for incorporating anti-oxidant diphenylamine into PAO feedstocks.

Useful diphenylamines include substituted and non-substituted species and may be represented by the following formula:

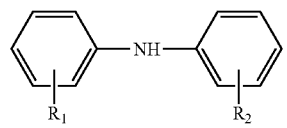

wherein $R_1$ and $R_2$ are, independently, a hydrogen or an alkyl group of 1 to 12 carbons or an aryl group of 1 to 12 carbons. A preferred species is unsubstituted, wherein both $R_1$ and $R_2$ are hydrogen. Useful substituted diphenylamines include N-phenyl-1-naphthylamine, N-phenyl-2-naphthylamine, and N,N'-diphenyl-p-phenylenediamine.

Further according to the present disclosure, there is a diphenylamine-functionalized poly-α-olefin product having the following structure:

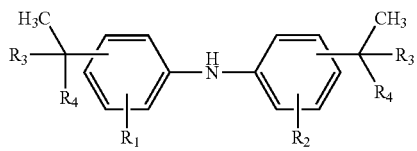

wherein R1 and R2 can be hydrogen or alkyl group of 1 to 12 carbons or an aryl group of 1 to 12 carbons and wherein R3 and R4 are, independently, an alkyl group of 8 to 30 carbons or an aryl group of 8 to 30 carbons.

The diphenylamine-functionalized PAOs of the present disclosure are particularly useful as antioxidants in PAO lubricant systems. The diphenylamine-functionalized PAOs can also be used as plasticizers for polyolefins, such as polypropylene and ethylene-propylene copolymers, as well as for engineering thermoplastics.

The following are examples of the present disclosure and are not to be construed as limiting.

EXAMPLES

Illustrative Example 1

The Alkylation of PAO Dimer with Diphenylamine Catalyzed by Engelhard Clay F-24 (25304-51)

20.7 g of PAO dimer (FW. 280, 0.074 mole), 2.5 g of diphenylamine (FW. 169.22, 0.015 mole) and 4.0 g of Engelhard clay F-24 catalyst were mixed up in a 100 ml round bottom flask. The reaction system was brought to 100° C. and kept stirring overnight (18 hours). The reaction mixture was filtrated and excess unreacted PAO dimer was removed by vacuum distillation at 5 mmHg at 160° C. 8.5 g of product (a mono-alkylation and di-alkylation mixture) was obtained. 13.9 g of unreacted PAO dimer was collected. The yield was almost quantitative based on diphenylamine, i.e., the diphenylamine was substantially consumed during the reaction.

The product was characterized using IR, NMR and GPC. The FTIR spectra of the starting PAO showed the vinyl double bond peak at 3069, 1644 and 888 cm$^{-1}$. After the diphenylamine reaction, the double bond peaks disappeared and new peaks appeared at 3450 and 1606 cm$^{-1}$ (see FIG. 1). The product was examined by carbon NMR to determine the composition of the copolymer. The $^{13}$C NMR results suggest that all the double bonds reacted during the diphenylamine reaction. A field desorption mass spectroscopy (FDMS) analysis of diphenylamine-alkylated PAO dimer showed m/e peak at 729.4 due to PAO dimer difunctionalized with DPA and m/e peak at 449.1 due to PAO dimer monofunctionalized with DPA.

The product of was evaluated in several performance tests versus the starting PAO. The kinematic viscosity (Kv) of the liquid product was measured using ASTM standards D445 and reported at temperatures of 100° C. (Kv at 100° C.) or 40° C. (Kv at 40° C.). The viscosity index (VI) was measured according to ASTM standard D2270 using the measured kinematic viscosities for each product. The details are shown in Table 1 below.

TABLE I

| Sample | VI | Viscosity (100° C.) | Viscosity (40° C.) |
|---|---|---|---|
| PAO dimmer (23526-60) | 119 | 2.1 | 6.4 |
| PAO-DPA (25304-51) | 120 | 6.4 | 37.5 |

The viscosity data suggests that DPA alkylation process converted non-lubricant PAO dimer into a lubricant product with viscosity of 6.4 cSt. The VI of the product is also high.

Pressure Differential Scanning Calorimetry (PDSC)

PDSC is a useful screening tool for measuring oxidative stability. PDSC is used to determine oxidation under heating conditions. A heating experiment measures the temperature at which oxidation initiates under oxygen pressure.

Figure 2:
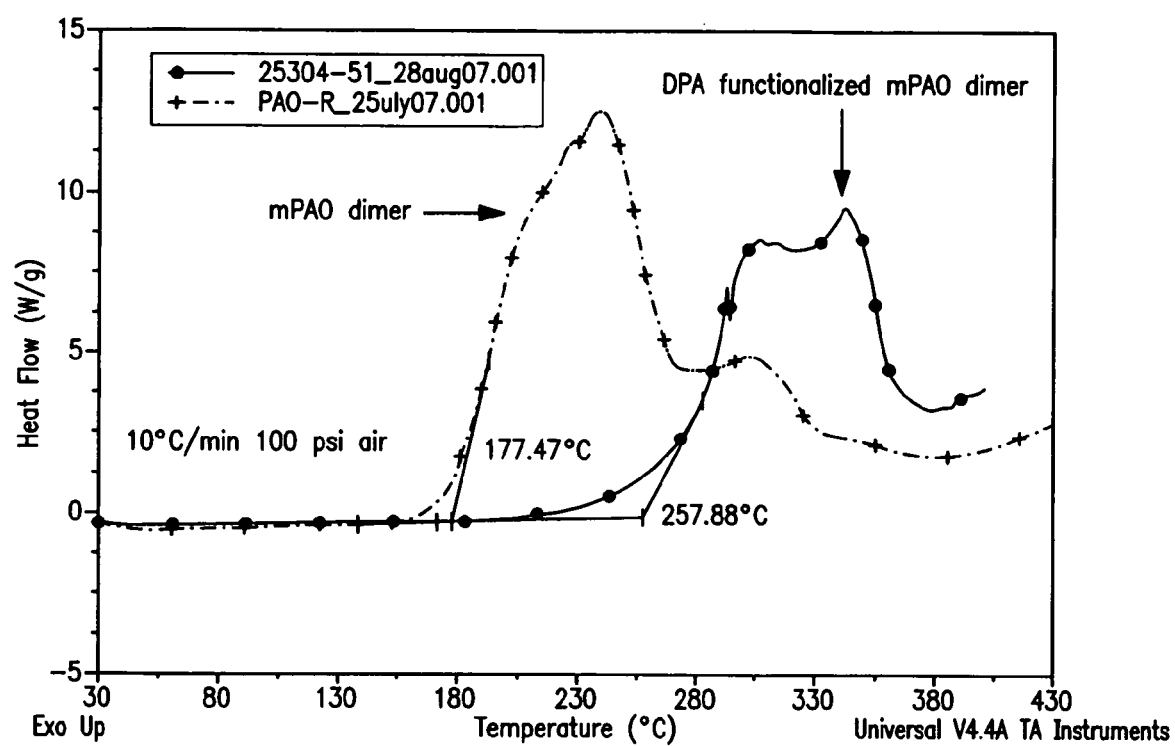
FIG. 2 is a representation of DSC heating data for the PAO dimer and the diphenylamine-functionalized PAO dimer of FIG. 1.

A DSC Model 2920 (TA instruments) with a pressure cell was used for the measurements. The cell is well calibrated for temperature (+/−0.3° C.) and heat flow (better than 1%) and checked for reproducibility daily with a QC standard for temperature and heat response. The heating measurements were carried out at a heating rate of 10° C./min using pressure of 100 psi in air. FIG. 2 shows the heating data obtained for the neat PAO dimer and the DPA-functionalized PAO dimer.

The heating-in-air data showed that oxidation of DPA-functionalized PAO occurs at 257° C. compared to PAO dimer, for which the oxidation occurred at 177° C. Thus, there is a substantial improvement in oxidation stability of the functionalized PAO. The DPA-functionalized PAO dimer can be co-blended with non-polar base stocks like PAO, Visom and GTL type fluids to improve solvency.

Illustrative Example 2

The Alkylation of PAO Dimer with Diphenylamine Catalyzed by IL (25304-53)

Ionic liquid catalyst (EMIM.Al$_2$Cl$_7$) was prepared by the following procedure: 2.8 g of EMIM.AlCl$_4$ ionic liquid (FW. 280, 0.01 mole) and 1.34 g of aluminum chloride (FW. 133.5, 0.01 mole) were mixed together and stirred to obtain a homogeneous mixture. FW=number average molecular weight.

8.85 g of PAO dimer (FW. 280, 0.0316 mole), 1.07 g of diphenylamine (FW. 169.22, 0.0063 mole) and 1.0 g of EMIM.Al$_2$Cl$_7$ were mixed up and heated to 100° C. with a heating mantle. The reaction system was kept stirring overnight. Reaction was monitored by TLC with hexane as the eluent. The reaction mixture was filtrated through celite. The ionic liquid was removed by washing with saturated NaHCO$_3$ (200 ml×3) and brine (200 ml) in hexane solution (200 ml). Excess unreacted PAO dimmer was removed by vacuum distillation at 5 mmHg and 160° C. 7.1 g of product (mono-alkylation and di-alkylation mixture) was obtained. 2.4 g of unreacted PAO dimmer was collected. The yield was almost quantitative based on diphenylamine. Judging from TLC, almost all the product was di-substituted or PAO oligomer-substituted.

Figure 3:
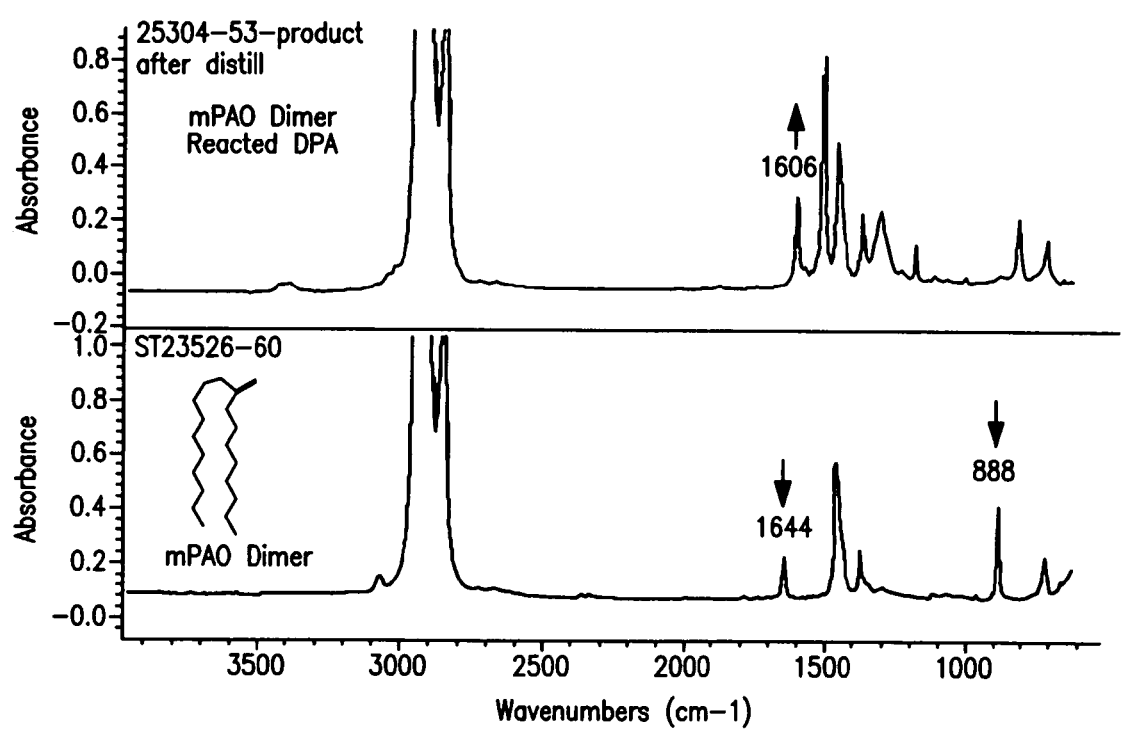
FIG. 3 is a representation of FTIR Spectra of a PAO Dimer and another diphenylamine-functionalized PAO dimer product of the present disclosure.
Figure 4:
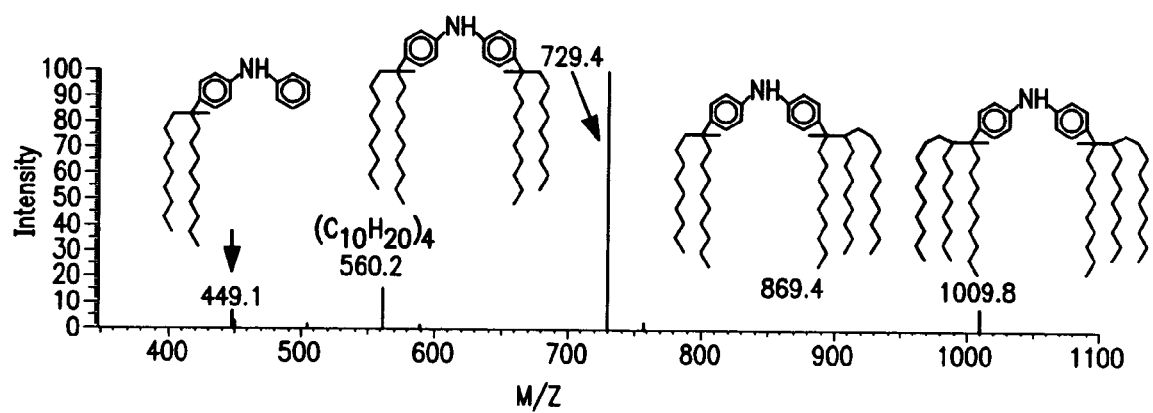
FIG. 4 is a representation of a field desorption mass spectroscopy (FDMS) analysis of the diphenylamine-functionalized PAO dimer product of FIG. 3.

The product was characterized using IR, NMR and GPC. The FTIR spectra of the starting PAO showed that vinyl double bond peaks at 3069, 1644 and 888 cm$^{-1}$. After the diphenylamine reaction, the double bond peaks disappeared and new peaks at 3450 and 1606 cm$^{-1}$ appeared (see FIG. 3). The product number for 510 is 25304-53 and for 509 is 25304-51. The product was examined by carbon NMR to determine the composition of the copolymer. The $^{13}$C NMR results suggest that all the double bonds reacted during the diphenylamine reaction. A field desorption mass spectroscopy (FDMS) analysis of diphenylamine-functionalized PAO dimer showed a major m/e peak at 729.4 due to PAO dimer difunctionalized with DPA and m/e peak at 449.1 due to PAO dimer monofunctionalized with DPA. The MS also showed peaks at 560.2 due to tetramer and peaks at 869.4 and 1009.8 due to possibly oligomerized and then alkylated PAO products (see FIG. 4). The mass spectrum x-axis in FIG. 4 refers to mass/charge ratio, while m/e refers to molecular ion peak.

The product was evaluated in several performance tests versus the starting PAO. The kinematic viscosity (Kv) of the liquid product was measured using ASTM standards D445 and reported at temperatures of 100° C. (Kv at 100° C.) or 40° C. (Kv at 40° C.). The viscosity index (VI) was measured according to ASTM standard D2270 using the measured kinematic viscosities for sample. The details are shown in the Table 2 below.

TABLE 2

| Sample | VI | Viscosity (100° C.) | Viscosity (40° C.) |
|---|---|---|---|
| PAO dimer (23526-60) | 119 | 2.1 | 6.4 |
| PAO-DPA (25304-53) | 118 | 12.1 | 96.5 |

The viscosity data suggest that DPA alkylation process converts the non-lubricant PAO dimer into a high viscosity lubricant product with viscosity of 12.1 cSt. The VI of the product is also high.

Figure 5:
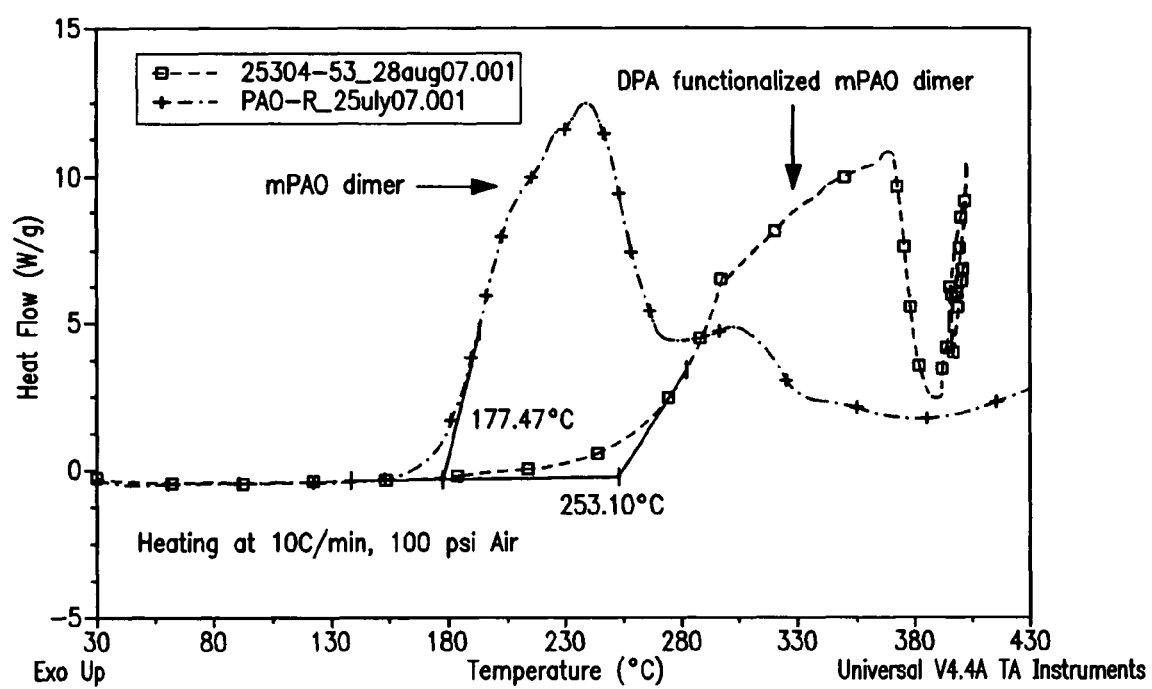
FIG. 5 is a representation of DSC heating data for the PAO dimer and the diphenylamine-functionalized PAO dimer of FIG. 3.

A DSC Model 2920 (TA instruments) with a pressure cell was used for PDSC measurements. The cell is well calibrated for temperature (+/−0.3° C.) and heat flow (better than 1%) and checked for reproducibility daily with a QC standard for temperature and heat response. The heating measurements were carried out at a heating rate of 10° C./min using pressure of 100 psi in air. FIG. 5 shows the heating data obtained for the neat PAO dimer and the product DPA functionalized PAO dimer.

The heating in air data showed that oxidation of diphenylamine (DPA)-functionalized PAO occurs at 253° C. compared to PAO dimer for which oxidation occurred at 177° C. Thus, there is a substantial improvement in oxidation stability of the functionalized PAO. The DPA-functionalized PAO dimer can be co-blended with non-polar base stocks like PAO, Visom and GTL type fluids to improve solvency.

Applicants have attempted to disclose all embodiments and applications of the disclosed subject matter that could be reasonably foreseen. However, there may be unforeseeable, insubstantial modifications that remain as equivalents. While the present disclosure has been described in conjunction with specific, exemplary embodiments thereof, it is evident that many alterations, modifications, and variations will be apparent to those skilled in the art in light of the foregoing description without departing from the spirit or scope of the present disclosure. Accordingly, the present disclosure is intended to embrace all such alterations, modifications, and variations of the above detailed description.

When numerical lower limits and numerical upper limits are listed herein, ranges from any lower limit to any upper limit are contemplated.

What is claimed is:

1. A process for making a diphenylamine-functionalized poly-α-olefin, comprising: reacting an amount of a poly-α-olefin having a terminal double bond with a diphenylamine in the presence of a catalyst, wherein the poly-α-olefin has a number average molecular weight of 120 to 600, wherein the ratio of poly-α-olefin having a terminal double bond to diphenylamine is 1.0:1.0 to 10.0:1.0, and wherein the diphenylamine is represented by the following structure:

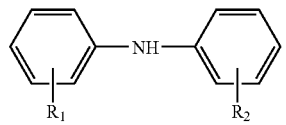

wherein $R_1$ and $R_2$ are, independently, selected from the group consisting of a hydrogen, an alkyl group of 1 to 12 carbons, and an aryl group of 1 to 12 carbons, and wherein the reacting step includes oligomerizing the poly-α-olefin followed by alkylating the diphenylamine with the oligomerized poly-α-olefin.

2. The process of claim 1, wherein the catalyst is selected from the group consisting of a Friedel-Crafts catalyst, a protonic acid catalyst, an ionic liquid catalyst, and combinations thereof.

3. The process of claim 1, wherein the catalyst is a Friedel-Crafts catalyst.

4. The process of claim 1, wherein the catalyst is an ionic liquid catalyst.

5. The process of claim 4, wherein the ionic liquid catalyst has an acid component selected from the group consisting of one or more aluminum halides, one or more alkyl aluminum halides, and combinations thereof.

6. The process of claim 4, wherein the ionic liquid catalyst has an acid component selected from the group consisting of aluminum trichloride, aluminum bromide, iron (III) chloride, zinc chloride, and boron trifluoride.

7. The process of claim 4, wherein the ionic liquid catalyst has an ionic liquid component selected from the group consisting of 1-Butyl-3-methylimidazolium hexafluorophosphate [bmim$^+$][PF$_6^-$], trihexyl (tetradecyl) phosphonium chloride [thtdPh$^+$][Cl$^-$], 1-ethyl-3-methylimidazolium methanesulfonate [emim$^+$][CH$_3$SO$_3^-$], 1-Ethyl-3-methylimidazolium thiocyanate [emim$^+$][SCN$^-$], choline salicylate, 1-ethyl-3-methylimidazolium tetrachloroaluminate [emim$^+$][AlCl$_4^-$], 1-Butyl-3-methylimidazolium hexafluorophosphate [bmim][PF$_6^-$], 1-Hexyl-3-methylimidazolium dioctylsulfosuccinate [hmim][doss$^-$], 1-Hexyl-3-methylimidazolium hexafluoroborate [hmim][BF$_4^-$], 1-Hexyl-3-methylimidazolium hexafluorophosphate [hmim][PF$_6^-$], tetrabutyl ammonium dioctylsulfosuccinate [tbam][doss$^-$], tetrabutyl phosphonium dioctylsulfosuccinate [tbPh][doss$^-$], tributyl (tetradecyl) phosphonium dodecylbenzenesulfonate [tbtdPh][dbs$^-$]; tributyl (tetradecyl) phosphonium methanesulfonate [tbtdPh][mes$^-$], trihexyl (tetradecyl) phosphonium bis(trifluoromethane) sulfonylimide [thtdPh][Tf$_2$N$^-$], trihexyl (tetradecyl) phosphonium chloride [thtdPh][Cl$^-$], trihexyl (tetradecyl) phosphonium decanoate [thtdPh][deca$^-$], trihexyl (tetradecyl) phosphonium dodecylbenzenesulfonate [thtdPh][dbs$^-$]; and trihexyl (tetradecyl) phosphonium methanesulfonate [thtdPh][mes$^-$].

8. The process of claim 7, wherein the ionic liquid component is selected from the group consisting of 1-Butyl-3-methylimidazolium hexafluorophosphate and trihexyl (tetradecyl) phosphonium chloride.

9. The process of claim 1, wherein the $R_1$ and $R_2$ are both hydrogen.

10. The process of claim 1, wherein the poly-α-olefin having a terminal double bond has a number average molecular weight of 150 to 400.

11. The process of claim 1, wherein the poly-α-olefin having a terminal double bond has a number average molecular weight of 160 to 280.

12. The process of claim 1, wherein the molar ratio of a poly-α-olefin having a terminal double bond to diphenylamine is in the range of 1.0:1.0 to 4.0:1.0.

13. The process of claim 1, wherein the molar ratio of a poly-α-olefin having a terminal double bond to diphenylamine is in the range of 1.25:1.0 to 3.0:1.0.

14. The process of claim 1, wherein the molar ratio of a poly-α-olefin having a terminal double bond to diphenylamine is in the range of 1.5:1.0 to 2.8:1.0.

15. A diphenylamine-functionalized poly-α-olefin of the following structure:

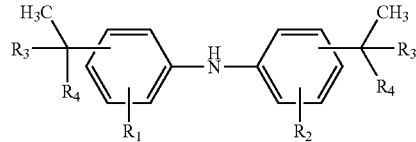

wherein $R_1$ and $R_2$ are, independently, selected from the group consisting of hydrogen, an alkyl group of 1 to 12 carbons, and an aryl group of 1 to 12 carbons and wherein $R_3$ and $R_4$ are, independently, selected from the group consisting of a linear alkyl group of 8 to 30 carbons and an aryl group of 8 to 30 carbons, and wherein the diphenylamine-functionalized poly-α-olefin is a liquid at room temperature with a kinematic viscosity at 100° C. of at least 6.4 centistokes.

* * * * *